United States Patent
Zheng et al.

(10) Patent No.: US 9,597,467 B2
(45) Date of Patent: Mar. 21, 2017

(54) AUTOMATIC PATIENT SYNCHRONY ADJUSTMENT FOR NON INVASIVE VENTILATION

(71) Applicant: KONINKLIJKE PHILIPS N.V., Eindhoven (NL)

(72) Inventors: Han Zheng, Carlsbad, CA (US); Samir Ahmad, San Diego, CA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 276 days.

(21) Appl. No.: 14/356,535

(22) PCT Filed: Nov. 7, 2012

(86) PCT No.: PCT/IB2012/056214
§ 371 (c)(1),
(2) Date: May 6, 2014

(87) PCT Pub. No.: WO2013/068933
PCT Pub. Date: May 16, 2013

(65) Prior Publication Data
US 2014/0283833 A1    Sep. 25, 2014

Related U.S. Application Data

(60) Provisional application No. 61/556,325, filed on Nov. 7, 2011.

(51) Int. Cl.
*A61M 16/00*     (2006.01)
*A61B 5/087*     (2006.01)
*A61B 5/085*     (2006.01)

(52) U.S. Cl.
CPC ......... *A61M 16/0003* (2014.02); *A61B 5/087* (2013.01); *A61M 16/0051* (2013.01);
(Continued)

(58) Field of Classification Search
CPC ... A61B 5/002; A61B 5/0022; A61B 5/02055; A61B 5/021; A61B 5/036; A61B 5/0476; A61B 5/053; A61B 5/08; A61B 5/085; A61B 5/087; A61B 5/1118; A61B 5/14551; A61B 5/165; A61B 5/411;
(Continued)

(56) References Cited

U.S. PATENT DOCUMENTS 5,316,009 A * 5/1994 Yamada ................ A61B 5/087
                                                 128/204.23
5,876,352 A   3/1999 Weismann
(Continued)

FOREIGN PATENT DOCUMENTS

CN    101484202 A    7/2009
CN    102164540 A    8/2011
(Continued)

*Primary Examiner* — Annette Dixon

(57) ABSTRACT

Automatically adjusting the trigger sensitivity of a respiratory therapy system includes detecting errors that indicate the trigger sensitivity should be increased, as well as detecting errors that indicate the trigger sensitivity should be reduced. Error detection may be based on the determined muscle pressure of a subject during an inhalation, an attempted inhalation, and/or a suspected attempt of an inhalation.

12 Claims, 4 Drawing Sheets

(52) U.S. Cl.
CPC ...... *A61B 5/085* (2013.01); *A61M 2016/0021* (2013.01); *A61M 2016/0036* (2013.01); *A61M 2205/3303* (2013.01); *A61M 2205/50* (2013.01); *A61M 2205/502* (2013.01); *A61M 2205/52* (2013.01); *A61M 2230/46* (2013.01)

(58) Field of Classification Search
CPC ..... A61B 5/412; A61B 5/4519; A61B 5/4809; A61B 5/4866; A61B 5/6801; A61B 5/7267; A61B 5/742; A61M 16/00; A61M 16/0051; A61M 16/0057; A61M 16/0063; A61M 16/16; A61M 16/161; A61M 16/20; A61M 16/204; A61M 16/205; A61M 2016/0021; A61M 2016/0024; A61M 2016/0027; A61M 2016/0036; A61M 2016/0039; A61M 2016/0042; A61M 2016/1025; A61M 2205/15; A61M 2205/18; A61M 2205/332; A61M 2205/3365; A61M 2205/3368; A61M 2205/3553; A61M 2205/3584; A61M 2205/502; A61M 2205/505; A61M 2205/52; A61M 2205/702; A61M 2230/005; A61M 2230/06; A61M 2230/205; A61M 2230/40; A61M 2230/42; A61M 2230/43; A61M 2230/432; A61M 2230/435; A61M 2230/46; G06F 19/3475; G06F 19/3481; G09B 19/00

USPC ................. 128/204.18, 204.21, 204.23, 921; 600/300, 533
See application file for complete search history.

(56) References Cited

U.S. PATENT DOCUMENTS

| | | |
|---|---|---|
| 2007/0028920 A1 | 2/2007 | Acker et al. |
| 2011/0029910 A1* | 2/2011 | Thiessen ............... A61M 16/00 715/771 |
| 2011/0237970 A1* | 9/2011 | Isaza ..................... A61B 5/036 600/533 |
| 2012/0145154 A1* | 6/2012 | Baloa Welzien ........ A61B 5/08 128/204.23 |
| 2013/0025597 A1* | 1/2013 | Doyle .................. A61M 16/00 128/204.23 |

FOREIGN PATENT DOCUMENTS

| | | | |
|---|---|---|---|
| EP | 0521515 A1 | 7/1992 | |
| EP | 1346743 A1 | 9/2003 | |
| WO | 9722377 A1 | 6/1997 | |
| WO | 0228460 A1 | 4/2002 | |
| WO | 2007131314 A1 | 11/2007 | |
| WO | 2009082295 A1 | 7/2009 | |
| WO | 2010036653 A1 | 4/2010 | |
| WO | 2010067244 A1 | 6/2010 | |
| WO | 2010121313 A1 | 10/2010 | |
| WO | WO2011/027242 A1 * | 3/2011 | ............... A61B 5/08 |
| WO | 2011044627 A1 | 4/2011 | |
| WO | 2013027137 A1 | 2/2013 | |

\* cited by examiner

AUTOMATIC PATIENT SYNCHRONY ADJUSTMENT FOR NON INVASIVE VENTILATION

CROSS-REFERENCE TO PRIOR APPLICATIONS

This application is the U.S. National Phase application under 35 U.S.C. §371 of International Application No. PCT/IB2012/056214, filed on Nov. 7, 2012, which claims the benefit of U.S. Provisional Patent Application No. 61/556,325, filed on Nov. 7, 2011. These applications are hereby incorporated by reference herein.

BACKGROUND

1. Field

The present disclosure pertains to systems and methods for providing respiratory therapy, and, in particular, for automatically adjusting the trigger sensitivity used to detect trigger events that indicate respiratory effort by a subject. The trigger events may be used to adjust the provided pressurized flow of breathable gas.

2. Description of the Related Art

It is well known that a patient (or hereinafter "a subject") may benefit from respiratory therapy, including but not limited to pressure support therapy. It is well known that in some forms of respiratory therapy, including but not limited to non-invasive ventilation, a subject may initiate one or more phases of a respiratory cycle. It is well known that phase synchronization between a subject and a respiratory therapy system and/or device, including but not limited to ventilators, are an important component of a subject's comfort during respiratory therapy, the therapy's effectiveness, and/or other therapeutic considerations. It is known that detecting the moment in time that a subject initiates an inhalation is commonly referred to as triggering.

SUMMARY

Accordingly, it is an object of one or more embodiments of the present invention to provide a respiratory therapy system. The system comprises a pressure generator configured to generate a pressurized flow of breathable gas for delivery to the airway of a subject; one or more sensors configured to generate one or more output signals conveying information related to one or more gas parameters of the pressurized flow of breathable gas; and one or more processors configured to execute computer program modules. The computer program modules include a trigger module configured to detect trigger events indicating respiratory effort by the subject based on the one or more output signals and one or more trigger parameters, wherein the one or more trigger parameters are adjustable to facilitate detection of the trigger events with different levels of trigger sensitivity; a muscle pressure module configured to determine a muscle pressure of the subject based on the one or more output signals; an error detection module configured to detect one or both of an ineffective trigger event and/or a false trigger event, wherein one or both detections by the error detection module are based on the determined muscle pressure; a sensitivity module configured to adjust the one or more trigger parameters to adjust the trigger sensitivity based on one or more detections by the error detection module; and a control module configured to control the pressure generator to adjust one or more gas parameters of the pressurized flow of breathable gas as a function of time in accordance with a respiratory therapy regime, wherein the respiratory therapy regime dictates adjustments to the one or more gas parameters based on the detected trigger events.

It is yet another aspect of one or more embodiments of the present invention to provide a method of providing respiratory therapy. The method comprises generating a pressurized flow of breathable gas for delivery to the airway of a subject; generating one or more output signals conveying information related to one or more gas parameters of the pressurized flow of breathable gas; detecting trigger events that indicate respiratory effort by the subject based on the one or more output signals and one or more trigger parameters, wherein the one or more trigger parameters are adjustable to facilitate detection of the trigger events with different levels of trigger sensitivity; determining a muscle pressure of the subject based on the one or more output signals; detecting one or both of an ineffective trigger event and/or a false trigger event, wherein one or both detections are based on the determined muscle pressure; adjusting the one or more trigger parameters to adjust the trigger sensitivity based on one or both of the detected ineffective trigger and/or the detected false trigger; and adjusting one or more gas parameters of the pressurized flow of breathable gas as a function over time in accordance with a respiratory therapy regime, wherein the respiratory therapy regime dictates adjustments to the one or more gas parameters based on the detected trigger events.

It is yet another aspect of one or more embodiments to provide a system configured to provide respiratory therapy. The system comprises means for generating a pressurized flow of breathable gas for delivery to the airway of a subject; means for generating one or more output signals conveying information related to one or more gas parameters of the pressurized flow of breathable gas; means for detecting trigger events that indicate respiratory effort by the subject based on the one or more output signals and one or more trigger parameters, wherein the one or more trigger parameters are adjustable to facilitate detection of the trigger events with different levels of trigger sensitivity; means for determining a muscle pressure of the subject based on the one or more output signals; means for detecting one or both of an ineffective trigger event and/or a false trigger event, wherein one or both detections are based on the determined muscle pressure; means for adjusting the one or more trigger parameters to adjust the trigger sensitivity based on one or both of the detected ineffective trigger and/or the detected false trigger; and means for adjusting one or more gas parameters of the pressurized flow of breathable gas as a function over time in accordance with a respiratory therapy regime, wherein the respiratory therapy regime dictates adjustments to the one or more gas parameters based on the detected trigger events.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

Figure 1:
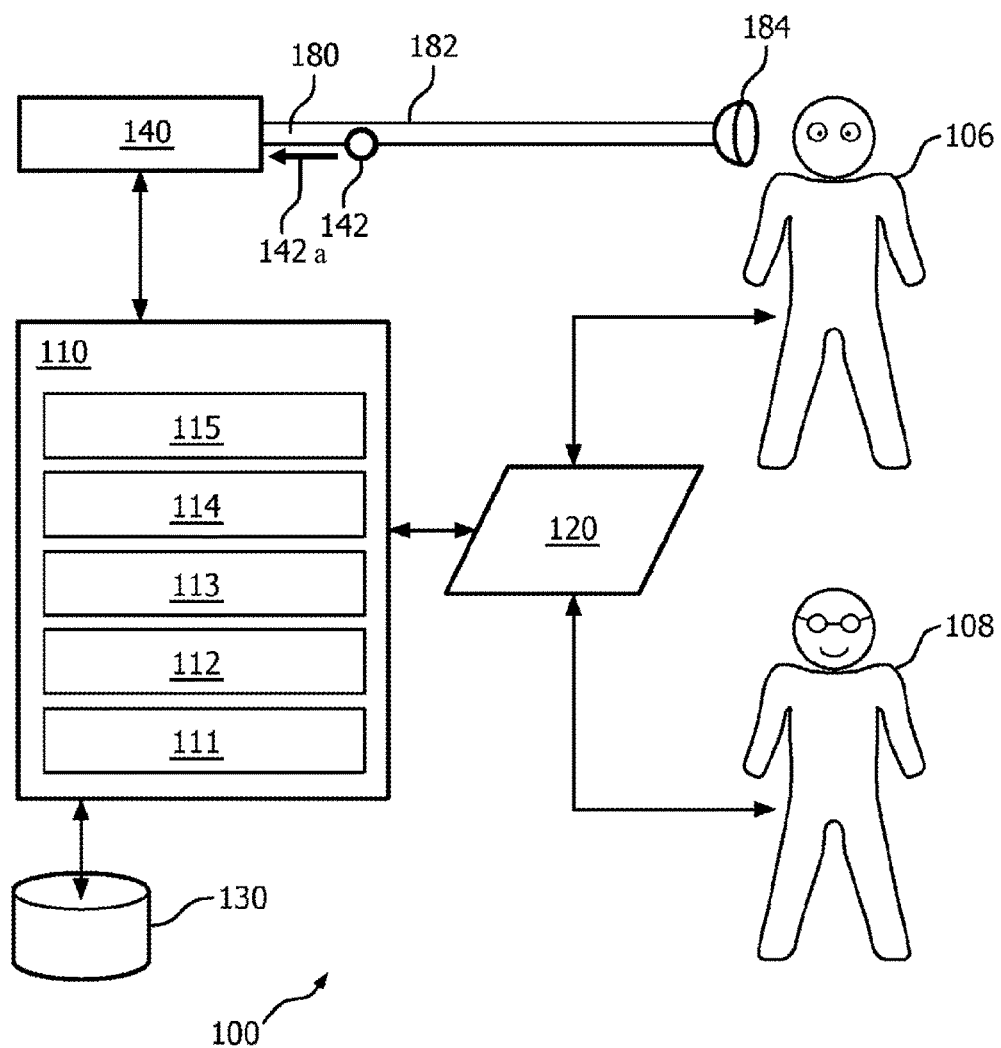
FIG. 1 schematically illustrates a system configured to provide respiratory therapy according to one or more embodiments.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 schematically illustrates a system 100 configured to provide respiratory therapy according to one or more embodiments. System 100 may be implemented as, integrated with, and/or operating in conjunction with a respiratory therapy device. System 100 may automatically adjust the trigger sensitivity used to detect trigger events that indicate respiratory effort by a subject and that are used to adjust one or more gas parameters governing the provision and/or delivery of a pressurized flow of breathable gas to a subject in accordance with a respiratory therapy regime. The respiratory therapy regime may dictate adjustments to the one or more gas parameters of the pressurized flow of breathable gas. Adjustments may be based on the detected trigger events. For example, after a trigger event is detected, a subsequently initiated change in the pressurized flow of breathable gas, such as, e.g., to support an inhalation, may be implemented. The respiratory therapy regime may dictate, e.g., one or more of a target inhalation pressure and/or pressure difference with a current pressure, a target tidal volume, a target inhalation duration, a target rate of inhalation pressure change and/or inhalation flow change, and/or other (gas) parameters of the pressurized flow of breathable gas. Any of these parameters may be adjusted based on one or more of environmental variables, time of day, progress of the respiratory therapy (such as, e.g., determined by measurements of breathing parameters and/or respiratory events), performance of any equipment and/or components thereof, feedback from the subject, and/or other considerations. Adjustments may be based on predetermined goals and/or targets for one or more respiratory parameters of the subject. For example, a respiratory therapy regime may be designed to gradually increase the total lung capacity of a subject over the span of multiple days or weeks.

System 100 includes one or more of a pressure generator 140, one or more sensors 142, an electronic storage 130, a user interface 120, one or more processors 110, a trigger module 111, a muscle pressure module 112, an error detection module 113, a sensitivity module 114, a control module 115, and/or other components.

Pressure generator 140 of system 100 may be integrated, combined, or connected with a ventilator and/or (positive) airway pressure device (PAP/CPAP/BiPAP®/etc.) and configured to provide a pressurized flow of breathable gas for delivery to the airway of a subject 106, e.g. via subject interface 180. Subject 106 may initiate one or more phases of respiration. Pressure support may be implemented as a higher and lower positive pressure of a (multi-level) PAP device. For example, to support inspiration, the pressure of the pressurized flow of breathable gas may be adjusted to an inspiratory positive airway pressure, or IPAP. Alternatively, and/or simultaneously, to support expiration, the pressure of the pressurized flow of breathable gas may be adjusted to an expiratory positive airway pressure, or EPAP. Other schemes for providing respiratory support through the delivery of the pressurized flow of breathable gas are contemplated, including, but not limited to, assist/control and/or spontaneous ventilation modes, as well as pressure control modes, volume control modes, pressure support modes, and/or other modes. Pressure generator 140 may be configured to adjust pressure levels, flow, volume, humidity, velocity, acceleration, and/or other parameters of the pressurized flow of breathable gas in substantial synchronization with the breathing cycle of the subject. In certain embodiments, pressure generator 140 is part of an airway pressure device configured to provide types of therapy other than positive airway support therapy.

A pressurized flow of breathable gas may be delivered from and/or via pressure generator 140 to the airway of subject 106 by subject interface 180. Subject interface 180 may include a conduit 182 and/or a subject interface appliance 184. Conduit 182 may be a flexible length of hose, or other conduit, that places subject interface appliance 184 in fluid communication with pressure generator 140. Conduit 182 may form a flow path through which the pressurized flow of breathable gas is communicated between subject interface appliance 184 and pressure generator 140.

Subject interface appliance 184 of system 100 in FIG. 1 may be configured to deliver the pressurized flow of breathable gas to or near the airway of subject 106. As such, subject interface appliance 184 may include any appliance suitable for this function. In one embodiment, pressure generator 140 is a dedicated ventilation device and subject interface appliance 184 is configured to be removably coupled with another interface appliance being used to deliver respiratory therapy to subject 106. For example, subject interface appliance 184 may be configured to engage with and/or be inserted into an endotracheal tube, a tracheotomy portal, and/or other interface appliances. In one embodiment, subject interface appliance 184 is configured to engage the airway of subject 106 without an intervening appliance. In this embodiment, subject interface appliance 184 may include one or more of an endotracheal tube, a nasal cannula, a tracheotomy tube, a nasal mask, a nasal/oral mask, a full face mask, a total face mask, a partial rebreathing mask, or other interface appliances that communicate a flow of gas with an airway of a subject. The present disclosure is not limited to these examples, and contemplates delivery of the pressurized flow of breathable gas to subject 106 using any subject interface.

Referring to FIG. 1, electronic storage 130 of system 100 comprises electronic storage media that electronically stores information. The electronic storage media of electronic storage 130 may include one or both of system storage that is provided integrally (i.e., substantially non-removable) with system 100 and/or removable storage that is removably connectable to system 100 via, for example, a port (e.g., a USB port, a FireWire port, etc.) or a drive (e.g., a disk drive, etc.). Electronic storage 130 may include one or more of optically readable storage media (e.g., optical disks, etc.), magnetically readable storage media (e.g., magnetic tape, magnetic hard drive, floppy drive, etc.), electrical charge-based storage media (e.g., EPROM, EEPROM, RAM, etc.), solid-state storage media (e.g., flash drive, etc.), and/or other electronically readable storage media. Electronic storage 130 may store software algorithms, information determined by processor 110, information received via user interface 120, and/or other information that enables system 100 to function properly. For example, electronic storage 130 may record or store one or more gas parameters and/or trigger parameters (as discussed elsewhere herein), information indicating whether the subject adequately complied with a therapy regimen, information indicating whether and/or when a respiratory event occurred, and/or other information. Electronic storage 130 may be a separate component within system 100, or electronic storage 130 may be provided integrally with one or more other components of system 100 (e.g., processor 110).

User interface 120 of system 100 is configured to provide an interface between system 100 and a user (e.g., a user 108, subject 106, a caregiver, a therapy decision-maker, etc.) through which the user can provide information to and receive information from system 100. This enables data, results, and/or instructions and any other communicable items, collectively referred to as "information," to be communicated between the user and system 100. An example of information that may be conveyed to subject 106 is a report detailing the changes in determined gas parameters throughout a period during which the subject is receiving (respiratory) therapy. An example of information that may be conveyed by subject 106 and/or user 108 is an initial trigger sensitivity to be used for system 100. Examples of interface devices suitable for inclusion in user interface 120 include a keypad, buttons, switches, a keyboard, knobs, levers, a display screen, a touch screen, speakers, a microphone, an indicator light, an audible alarm, and a printer. Information may be provided to subject 106 by user interface 120 in the form of auditory signals, visual signals, tactile signals, and/or other sensory signals.

By way of non-limiting example, user interface 120 may include a radiation source capable of emitting light. The radiation source may include, for example, one or more of at least one LED, at least one light bulb, a display screen, and/or other sources. User interface 120 may control the radiation source to emit light in a manner that conveys to subject 106 information related to breathing and/or the pressurized flow of breathable gas. Note that the subject and the user of system 100 may be one and the same person.

It is to be understood that other communication techniques, either hard-wired or wireless, are also contemplated herein as user interface 120. For example, in one embodiment, user interface 120 may be integrated with a removable storage interface provided by electronic storage 130. In this example, information is loaded into system 100 from removable storage (e.g., a smart card, a flash drive, a removable disk, etc.) that enables the user(s) to customize the implementation of system 100. Other exemplary input devices and techniques adapted for use with system 100 as user interface 120 include, but are not limited to, an RS-232 port, RF link, an IR link, modem (telephone, cable, Ethernet, internet or other). In short, any technique for communicating information with system 100 is contemplated as user interface 120.

Sensor(s) 142 of system 100 may be configured to generate output signals, e.g. output signal 142a, conveying measurements related to parameters of respiratory airflow or airway mechanics, including, but not limited to breath-by-breath estimations of lung resistance, lung compliance, and/or other airway mechanics. These parameters may include one or more of flow, (airway) pressure, humidity, velocity, acceleration, and/or other parameters. Sensor 142 may be in fluid communication with conduit 182 and/or subject interface appliance 184. For example, sensor 142 may comprise one or more of a flow sensor, a pressure sensor, a gas meter, a thermometer, a current sensor, an electro-optical sensor, an infra-red sensor, a proximity sensor, a hygrometer, and/or other sensors.

The illustration of sensor 142 including a single member in FIG. 1 is not intended to be limiting. In one embodiment sensor 142 includes a plurality of sensors operating as described. The one or more sensors 142 generate output signals conveying information related to gas parameters of the pressurized flow of breathable gas, and/or parameters associated with the state and/or condition of an airway of subject 106, the breathing of subject 106, the gas breathed by subject 106, and/or the delivery of the gas to the airway of subject 106. For example, a parameter may be related to a mechanical unit of measurement of a component of pressure generator 140 (or of a device that pressure generator 140 is integrated, combined, or connected with) such as rotor speed, motor speed, blower speed, fan speed, or a related measurement that may serve as a proxy for any of the previously listed parameters through a previously known and/or calibrated mathematical relationship. Resulting signals or information from sensor 142 may be transmitted to processor 110, user interface 120, electronic storage 130, and/or other components of system 100. This transmission may be wired and/or wireless.

Processor 110 of system 100 is configured to provide information processing capabilities in system 100. As such, processor 110 includes one or more of a digital processor, an analog processor, a digital circuit designed to process information, an analog circuit designed to process information, a state machine, and/or other mechanisms for electronically processing information. Although processor 110 is shown in FIG. 1 as a single entity, this is for illustrative purposes only. In some implementations, processor 110 includes a plurality of processing units.

As is shown in FIG. 1, processor 110 is configured to execute one or more computer program modules. The one or more computer program modules include one or more of trigger module 111, muscle pressure module 112, error detection module 113, sensitivity module 114, control module 115, and/or other modules. Processor 110 may be configured to execute modules 111, 112, 113, 114, and/or 115 by software; hardware; firmware; some combination of software, hardware, and/or firmware; and/or other mechanisms for configuring processing capabilities on processor 110.

It should be appreciated that although modules 111, 112, 113, 114, and 115 are illustrated in FIG. 1 as being co-located within a single processing unit, in implementations in which processor 110 includes multiple processing units, one or more of modules 111, 112, 113, 114, and/or 115 may be located remotely from the other modules. The description of the functionality provided by the different modules 111, 112, 113, 114, and/or 115 described below is for illustrative purposes, and is not intended to be limiting, as any of modules 111, 112, 113, 114, and/or 115 may provide more or less functionality than is described. For example, one or more of modules 111, 112, 113, 114, and/or 115 may be eliminated, and some or all of its functionality may be provided by other ones of modules 111, 112, 113, 114, and/or 115. Note that processor 110 may be configured to execute one or more additional modules that may perform some or all of the functionality attributed below to one of modules 111, 112, 113, 114, and/or 115.

One or more of the computer program modules of system 100 may be configured to determine one or more breathing parameters, gas parameters, and/or other parameters from output signals generated by sensor(s) 142. One or more gas parameters may be a function of, related to, and/or derived from measurements of one or more of (peak) flow, flow rate, (tidal) volume, pressure, temperature, humidity, velocity, acceleration, gas composition (e.g. concentration(s) of one or more constituents), thermal energy dissipated, (intentional) gas leak, and/or other measurements related to the (pressurized) flow of breathable gas. One or more breathing parameters may be derived from gas parameters and/or other output signals conveying measurements of the pressurized flow of breathable gas. The one or more breathing parameters may include one or more of respiratory rate, breathing period, inhalation time or period, exhalation time or period, respiration flow curve shape, transition time from inhalation to exhalation and/or vice versa, transition time from peak inhalation flow rate to peak exhalation flow rate and/or vice versa, respiration pressure curve shape, maximum proximal pressure drop (per breathing cycle and/or phase), fraction of inspired oxygen, and/or other breathing parameters.

Trigger module 111 of system 100 in FIG. 1 is configured to detect trigger events indicating respiratory effort by the subject. The trigger events are detected based on one or more of the one or more output signals generated by sensor 142, gas and/or breathing parameters determined from the one or more output signals, one or more trigger parameters, and/or other parameters. The indicated respiratory effort may be the onset of an inhalation phase, and/or other respiratory effort. The one or more trigger parameters may be adjustable to facilitate detection of trigger events with different levels of trigger sensitivity. For the same activity by the subject, e.g. a particular pattern or volume of inhalation flow, a first trigger event may be detected based on a smaller change in the one or more output signals, and/or a smaller change in one or more parameters determined from the output signals, compared to a second trigger event. In such a case, the first trigger event may be said to have been detected using a higher and/or increased level of trigger sensitivity, comparatively. Conversely, a first trigger event may be detected based on a larger change in the one or more output signals, and/or a larger change in one or more parameters determined from the output signal, compared to a second trigger event. In such a case, the first trigger event may be said to have been detected using a lower or reduced level of trigger sensitivity, comparatively.

Figure 2:
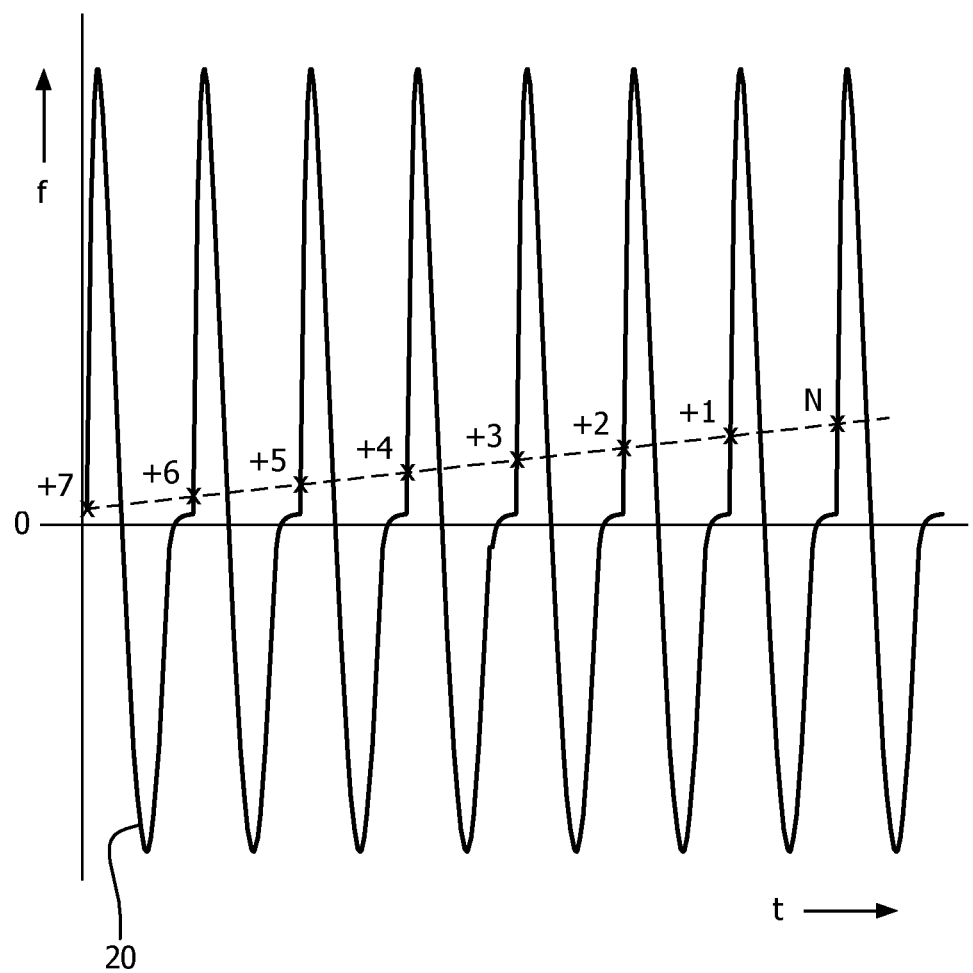
FIG. 2 illustrates a flow waveform related to one or more embodiments.

By way of illustration, FIG. 2 illustrates a flow waveform 20 for approximately eight respiratory cycles of a subject. The Y-axis depicts positive and negative flow at or near the airway of a subject during respiration. The X-axis depicts time. A default or "normal" setting for the trigger sensitivity may be depicted with a label "N". In FIG. 2. trigger sensitivity corresponds to a flow level. A trigger event in FIG. 2 is depicted by an "X" that marks the intersection of flow waveform 20 with the flow level that corresponds to a trigger sensitivity ranging from "N", for least sensitive, to "+7" for most sensitive. Note that a higher level of trigger sensitivity corresponds to a smaller change in the flow level of flow waveform 20 that is adequate for detection of a trigger event. The illustration in FIG. 2 of eight trigger sensitivity levels is not intended to be limiting, but is merely exemplary.

Trigger module 111 may use one or more of the following techniques to detect trigger events: wave shape triggering, volume triggering, and/or other techniques to detect trigger events indicating respiratory effort by the subject, particularly related to the inhalation phase.

Figure 3A:
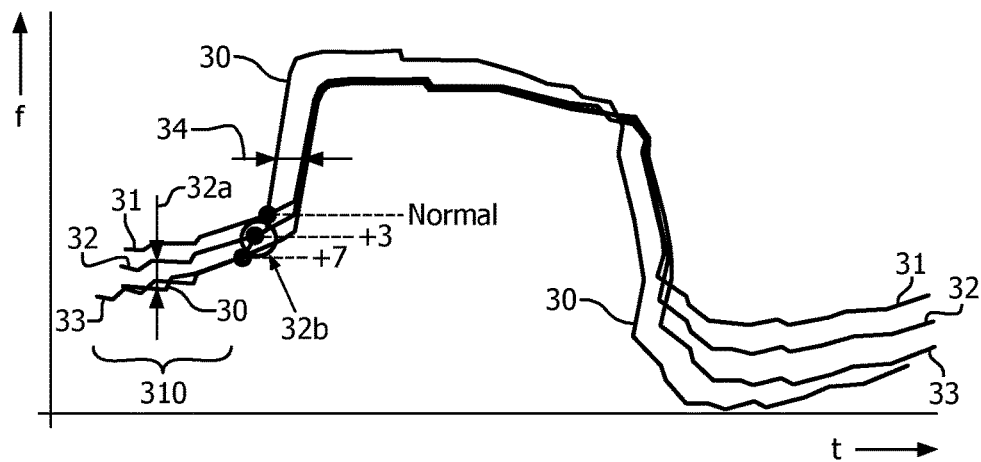
FIG. 3A-B illustrate flow waveforms related to trigger sensitivity in a system configured to provide respiratory therapy according to one or more embodiments.

Wave shape triggering of trigger module 111 may use one or more predetermined subject flow, e.g. a predicted subject flow shape. Note that the term "flow shape" is used interchangeably with "flow waveform." By way of illustration, FIG. 3A illustrates flow waveforms 30-33 related to wave shape triggering. Flow waveform 30 depicts the actual (estimated, measured, and/or determined) subject flow of subject 106. Predicted flow waveforms 31, 32, and 33 depict predicted subject flow shapes having different trigger sensitivities. Predicted flow waveforms 31, 32, and 33 may be characterized by intentionally being delayed by a delay amount 34 with respect to actual flow waveform 30. The delay may be applied comparative to the best fit, and/or any predetermined fit and/or match, for the predicted subject flow shape in relation to actual flow waveform 30. Delay amount 34 may be 200 ms, 300 ms, 400 ms, and/or other amounts of delay. Time period 310 corresponds to the end of an exhalation period. Predicted flow waveforms 31, 32, and 33 may be characterized by a higher flow than actual flow waveform 30 during, at least, time period 310. For example, predicted flow waveform 32 may have a flow offset 32a compared to actual flow waveform 30. Flow offsets may range from 1-20 LPM, or use another range of flow offsets. A smaller flow offset may correspond to a higher level of trigger sensitivity. Predicted flow waveform 31 corresponds to the default or "normal" trigger sensitivity as described in relation to FIG. 2. Referring to FIG. 3A, predicted flow waveform 32 may correspond to the "+3" trigger sensitivity. Predicted flow waveform 33 may correspond to the "+7" trigger sensitivity. The illustration and/or implication in FIG. 3A of eight trigger sensitivity levels is not intended to be limiting, but is merely exemplary. Trigger module 111 may detect a trigger event responsive to the actual flow waveform 30 intersecting with the predicted subject flow shape that corresponds to the current trigger sensitivity. For example, for a trigger sensitivity of "+3" the trigger event 32b may mark the intersection of predicted flow waveform 32 with actual flow waveform 30. Note that a higher level of trigger sensitivity may correspond to a smaller flow offset of the corresponding predicted subject flow shape. A smaller flow offset of the predicted subject flow shape may correspond to a smaller change in one or more output signals, and/or a smaller change in one or more parameters determined from the output signals that is adequate for detection of an intersection between the predicted subject flow shape and the actual flow waveform 30. For example, a smaller change of the flow level in the actual flow waveform 30 may correspond to a detected trigger event.

Figure 3B:
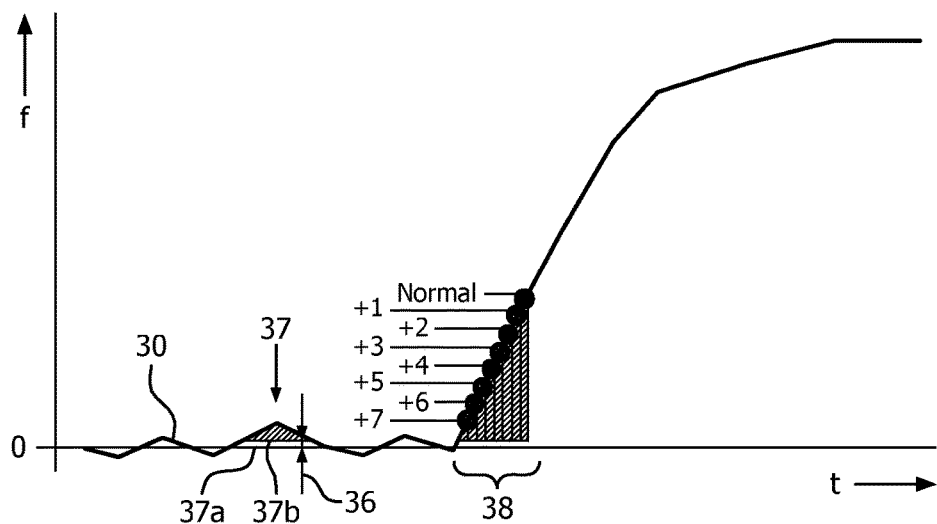

Volume triggering of trigger module 111 may detect a trigger event when a predetermined inhalation volume has been inspired by the subject. Detection may be responsive to the actual subject flow reaching at least a threshold amount of flow. The predetermined inhalation volume may be adjustable corresponding to the trigger sensitivity. Detection may be responsive to a determination that one or more of a predetermined phase in the respiratory cycle, a predetermined moment or event in the respiratory cycle, and/or another predetermined moment in time has occurred. For example, detection of an onset of an inhalation using volume triggering may be responsive to a determination that the preceding exhalation phase is beyond its peak negative flow. Other predetermined moments in time that indicate inhalation has not yet started are also contemplated. By way of illustration, FIG. 3B illustrates a flow waveform 30 related to volume triggering. Flow waveform 30 depicts the actual (estimated, measured, and/or determined) subject flow of subject 106. Flow threshold 36 depicts a positive flow threshold below which the inspired inhalation volume of a subject may be not measured and/or counted towards the predetermined inhalation volume used to detect a trigger event. Peak 37 of actual waveform 30 depicts a volume of flow that breaches flow threshold 36. Accordingly, a volume 37a below flow threshold 36 may be not measured and/or counted towards the predetermined inhalation volume used to detect a trigger event, unlike a volume 37b above flow threshold 36. Inhalation volume range 38 depicts a range of inhalation volumes that correspond to different trigger sensitivities, and thus different detected trigger events. Inhalation volume range 38 may range from 0.3 milliliter per minute (mLPM) to 6 mLPM, and/or any other suitable range. The illustration in FIG. 3B of eight trigger sensitivity levels is not intended to be limiting, but is merely exemplary. Note that a higher trigger sensitivity, up to and including a trigger sensitivity of "+7", corresponds to a smaller measured and/or counted inhalation volume that is adequate for detection of a trigger event.

Muscle pressure module 112 of system 100 in FIG. 1 is configured to determine a muscle pressure, or $P_{mus}$, of the subject based on one or more of the output signals generated by sensor 142. Using an active lung model, $P_{mus}$ may be determined by solving the following equation: $P_{mus}=P-(R \cdot Q/11000+V/C+P_0)$, where the unit of pressure may be cmH$_2$O, P may be the airway pressure of the subject, Q may be the subject flow, V may be subject volume in ml, which may be obtained independently, e.g., for each breath. R may be the lung resistance and C may be the lung compliance. By obtaining, estimating, and/or determining the proximal (or airway) pressure of the subject (e.g., at the start of an inhalation), the subject flow, and the pressure $P_0$ at the end of an exhalation directly following the inhalation, lung compliance and lung resistance may be determined, calculated and/or estimated, using the formula above. Methods and systems for determining $P_{mus}$, e.g. using an active lung model, are disclosed in U.S. Patent Application No. 61/527,186, filed Aug. 25, 2011, titled "Non-Invasive Ventilation Measurement," by at least one or more of the same inventors, which is hereby incorporated by reference herein in its entirety.

Error detection module 113 is configured to detect one or both of an ineffective trigger event and/or a false trigger event. Error detection may be based on the muscle pressure as determined by muscle pressure module 112.

Detection of an ineffective, or missing, trigger event by error detection module 113 may occur when at least some diaphragmatic effort of the subject has been detected, an attempt by the subject to breathe in has been detected, and/or an initiation by the subject of an inhalation has been detected, without an occurrence of a detection of a trigger event. An ineffective trigger event may be characterized by a negative oscillation of the subject's muscle pressure $P_{mus}$, which fails to be followed by a peak of airway pressure at, e.g., the predetermined IPAP value. An ineffective trigger event may be determined by a combination of the following three detected conditions: i) a subject flow is determined to be greater than a predetermined flow threshold of 0.5 LPM, 1.0 LPM, 2.0 LPM, and/or another flow threshold, ii) the maximum inhalation pressure is determined to be less than a predetermined pressure threshold of, e.g., the average between predetermined IPAP and EPAP values, and/or another predetermined value, and iii), the maximum inhalation muscle pressure $|P_{mus}|_{max}$ (e.g. during an inhalation or attempted inhalation) is determined to be greater than a predetermined muscle pressure threshold of, e.g., 0.5 cmH$_2$O, 1.0 cmH$_2$O, 2.0 cmH$_2$O, and/or another predetermined muscle pressure threshold. An ineffective trigger event may be determined by fewer detected conditions, and/or may include one or more additional detected conditions. For example, detection of an ineffective trigger event may take the most recent number of breathing cycles into account, or the previous detections of trigger events and/or errors of the most recent 30 seconds, one minute, and/or other predetermined period of time. Detection of an ineffective trigger event may be based on a statistical analysis of a recent history of trigger events and/or errors to determine a trend and/or an anomaly.

Detection of a false trigger event by error detection module 113 may occur when a subject has little or no diaphragmatic effort has been detected, little or no attempt to breathe in has been detected, and/or little or no initiation of an inhalation has been detected, but the occurrence of a trigger event is detected nonetheless. Such an error may be caused by random noise in the (respiratory) circuit, water in the circuit, muscle contractions and/or spasms, leaks in the circuit, cardiac oscillation, and/or other causes. A false trigger event may be determined by a combination of the following two detected conditions: i) the maximum inhalation pressure is determined to be greater than a predetermined pressure threshold of, e.g., the average between predetermined IPAP and EPAP values, and/or another predetermined value, and ii) the maximum inhalation muscle pressure $|P_{mus}|_{max}$ (e.g. during an inhalation or attempted inhalation) is determined to be less than a predetermined muscle pressure threshold of, e.g., 0.5 cmH$_2$O, 1.0 cmH$_2$O, 2.0 cmH$_2$O, and/or another predetermined muscle pressure threshold. A false trigger event may be determined by fewer detected conditions, and/or may include one or more additional detected conditions. For example, detection of a false trigger event may take the most recent number of breathing cycles into account, or the previous detections of trigger events and/or errors of the most recent 30 seconds, one minute, and/or other predetermined period of time. Detection of a false trigger event may be based on a statistical analysis of a recent history of trigger events and/or errors to determine a trend and/or an anomaly.

Sensitivity module 114 is configured to adjust one or more trigger parameters to adjust the trigger sensitivity. Adjustments by sensitivity module 114 may be based on one or more detections by error detection module 113, and/or by multiple such detections over a predetermined time period. In some embodiments, sensitivity module 114 may reduce the trigger sensitivity responsive to a determination that a quota (e.g. a predetermined threshold) for detections of false trigger events has been reached. Alternatively, and/or simultaneously, sensitivity module 114 may increase the trigger sensitivity responsive to a determination that a quota (e.g. a predetermined threshold) for detections of ineffective trigger events has been reached. Such quotas may be based on one or more of a sliding window of an observation period, the breathing rate of the subject, manually entered settings, personal preferences, adjustable sample times, and/or other values. Sensitivity module 114 may determine automatically and/or autonomously, whether or how to adjust the trigger sensitivity based, at least in part, on detections from trigger module 111 and/or error detection module 113.

Control module 115 is configured to control pressure generator 140 to adjust one or more gas parameters of the pressurized flow of breathable gas as a function over time in accordance with a respiratory therapy regime. The respiratory therapy regime may dictate adjustments to the one or more gas parameters based on the detected trigger events. For example, when a trigger event is detected, control module 115 may adjust one or more gas parameters of the pressurized flow of breathable gas such that a predetermined and/or prescribed inhalation positive airway pressure (or IPAP) is delivered to the airway of the subject. Alternatively, and/or simultaneously, the respiratory therapy regime may dictate, e.g., how and when to transition to the exhalation phase. For example, control module 115 may adjust one or more gas parameters of the pressurized flow of breathable gas such that a predetermined and/or prescribed exhalation positive airway pressure (or EPAP) is delivered to the airway of the subject.

Figure 4:
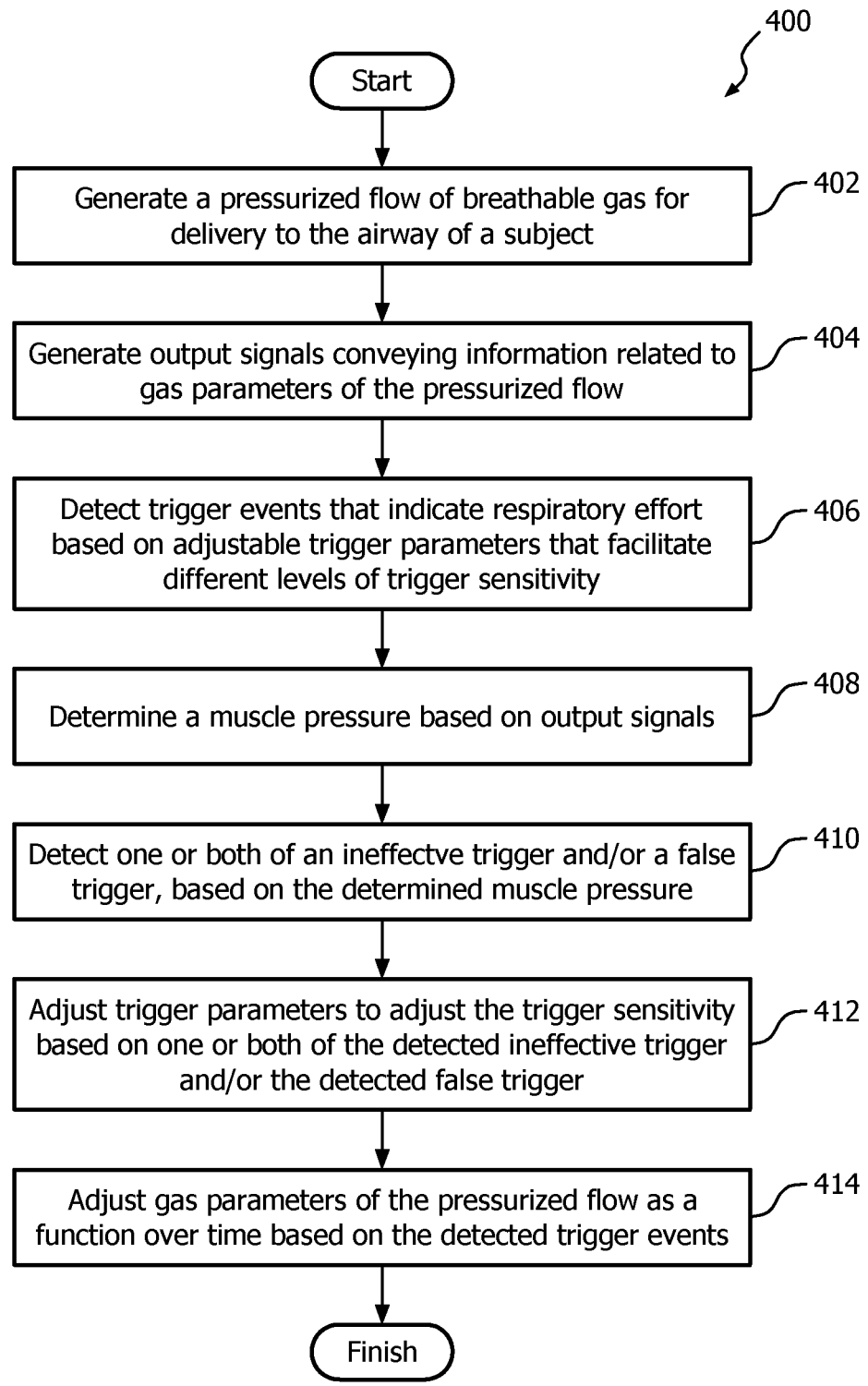
FIG. 4 illustrates a method for providing respiratory therapy according to one or more embodiments.

FIG. 4 illustrates a method 400 for providing respiratory therapy. The operations of method 400 presented below are intended to be illustrative. In some embodiments, method 400 may be accomplished with one or more additional operations not described, and/or without one or more of the operations discussed. Additionally, the order in which the operations of method 400 are illustrated in FIG. 4 and described below is not intended to be limiting. In some embodiments, method 400 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 400 in response to instructions stored electronically on an electronic storage medium. The one or more processing devices may include one or more devices configured through hardware, firmware, and/or software to be specifically designed for execution of one or more of the operations of method 400.

At an operation 402, a pressurized flow of breathable gas for delivery to the airway of a subject is generated. In one embodiment, operation 402 is performed by a pressure generator similar to or substantially the same as pressure generator 140 (shown in FIG. 1 and described above).

At an operation 404, one or more output signals are generated that convey information related to gas parameters of the pressurized flow of breathable gas. In one embodiment, operation 404 is performed by a sensor similar to or substantially the same as sensor 142 (shown in FIG. 1 and described above).

At an operation 406, one or more trigger events that indicate respiratory effort by the subject are detected based on the one or more output signals and one or more trigger parameters. The one or more trigger parameters are adjustable to facilitate detection of the trigger events with different levels of trigger sensitivity. In one embodiment, operation 406 is performed by a trigger module similar to or substantially the same as trigger module 111 (shown in FIG. 1 and described above).

At an operation 408, a muscle pressure of the subject is determined based on the one or more output signals. In one embodiment, operation 408 is performed by a muscle pressure module similar to or substantially the same as muscle pressure module 112 (shown in FIG. 1 and described above).

At an operation 410, one or both of an ineffective trigger and/or a false trigger is detected, based on the determined muscle pressure. In one embodiment, operation 410 is performed by an error detection module similar to or substantially the same as error detection module 113 (shown in FIG. 1 and described above).

At an operation 412, one or more trigger parameters are adjusted to adjust the trigger sensitivity based on the one or more detections by an error detection module. In one embodiment, operation 412 is performed by a sensitivity module similar to or substantially the same as sensitivity module 114 (shown in FIG. 1 and described above), in conjunction with an error detection module similar to or substantially the same as error detection module 113 (shown in FIG. 1 and described above).

At an operation 414, one or more gas parameters of the pressurized flow of breathable gas are adjusted, over time, in accordance with a respiratory therapy regime. The respiratory therapy regime dictates adjustments to the one or more gas parameters based on the detected triggers. In one embodiment, operation 414 is performed by a control module similar to or substantially the same as control module 115 (shown in FIG. 1 and described above).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A respiratory therapy system comprising:
  a pressure generator configured to generate a pressurized flow of breathable gas for delivery to the airway of a subject;
  one or more sensors configured to generate one or more output signals conveying information related to one or more gas parameters of the pressurized flow of breathable gas; and
  one or more processors configured to execute computer program modules, the computer program modules comprising:
  a trigger module configured to detect trigger events indicating respiratory effort by the subject based on the one or more output signals and one or more trigger parameters, wherein the one or more trigger parameters are adjustable to facilitate detection of the trigger events with different levels of trigger sensitivity;
a muscle pressure module configured to determine a muscle pressure of the subject using the one or more output signals, wherein the muscle pressure is determined based on per-breath estimations of a dynamic lung resistance and a dynamic lung compliance, wherein the per-breath estimations reflect an active lung model;
an error detection module configured to detect one or both of an ineffective trigger event and/or a false trigger event, wherein one or both detections by the error detection module are based on the determined muscle pressure;
a sensitivity module configured to adjust the one or more trigger parameters to adjust the trigger sensitivity based on one or more detections by the error detection module; and
a control module configured to control the pressure generator to adjust one or more gas parameters of the pressurized flow of breathable gas as a function of time in accordance with a respiratory therapy regime, wherein the respiratory therapy regime dictates adjustments to the one or more gas parameters based on the detected trigger events.

2. The system of claim 1, wherein the trigger module is configured to detect trigger events by one or both of:
a detection of an intersection of an actual subject flow with a predetermined subject flow, and/or
a detection of a predetermined inhalation volume having been inspired by the subject after a predetermined moment in time.

3. The system of claim 1, wherein detection of the ineffective trigger event is further based on a comparison of a subject flow with a predetermined flow threshold, and wherein detection of the false trigger event is further based on a comparison of an airway pressure with a predetermined pressure threshold.

4. The system of claim 1, wherein the sensitivity module reduces the trigger sensitivity responsive to a determination that a first quota for detections of false trigger event has been reached, and wherein the sensitivity module increases the trigger sensitivity responsive to a determination that a second quota for detections of ineffective trigger events has been reached.

5. A method of providing respiratory therapy, the method comprising;
generating a pressurized flow of breathable gas for delivery to the airway of a subject; generating one or more output signals conveying information related to one or more gas parameters of the pressurized flow of breathable gas;
detecting trigger events that indicate respiratory effort by the subject based on the one or more output signals and one or more trigger parameters, wherein the one or more trigger parameters are adjustable to facilitate detection of the trigger events with different levels of trigger sensitivity;
determining a muscle pressure of the subject using the one or more output signals, wherein the muscle pressure is determined based on per-breath estimations of a dynamic lung resistance and a dynamic lung compliance, wherein the per-breath estimations reflect an active lung model;
detecting one or both of an ineffective trigger event and/or a false trigger event, wherein one or both detections are based on the determined muscle pressure;
adjusting the one or more trigger parameters to adjust the trigger sensitivity based on one or both of the detected ineffective trigger event and/or the detected false trigger event; and
adjusting one or more gas parameters of the pressurized flow of breathable gas as a function over time in accordance with a respiratory therapy regime, wherein the respiratory therapy regime dictates adjustments to the one or more gas parameters based on the detected trigger events.

6. The method of claim 5, wherein detecting trigger events includes one or both of:
detecting an intersection of an estimated subject flow with a predicted subject flow, and/or
detecting inspiration of a predetermined inhalation volume by the subject after a predetermined moment in time.

7. The method of claim 5, wherein detection of the ineffective trigger event is further based on a comparison of a subject flow with a predetermined flow threshold, and wherein detection of the false trigger event is further based on a comparison of an airway pressure with a predetermined pressure threshold.

8. The method of claim 5, wherein adjusting the trigger sensitivity includes:
reducing the trigger sensitivity responsive to a determination that a first quota for detections of false trigger events has been reached, and
increasing the trigger sensitivity responsive to a determination that a second quota for detections of ineffective trigger events has been reached.

9. A system configured to provide respiratory therapy, the system comprising:
means for generating a pressurized flow of breathable gas for delivery to the airway of a subject;
means for generating one or more output signals conveying information related to one or more gas parameters of the pressurized flow of breathable gas;
means for detecting trigger events that indicate respiratory effort by the subject based on the one or more output signals and one or more trigger parameters, wherein the one or more trigger parameters are adjustable to facilitate detection of the trigger events with different levels of trigger sensitivity;
means for determining a muscle pressure of the subject using the one or more output signals, wherein the muscle pressure is determined based on per-breath estimations of a dynamic lung resistance and a dynamic lung compliance, wherein the per-breath estimations reflect an active lung model;
means for detecting one or both of an ineffective trigger event and/or a false trigger event, wherein one or both detections are based on the determined muscle pressure;
means for adjusting the one or more trigger parameters to adjust the trigger sensitivity based on one or both of the detected ineffective trigger event and/or the detected false trigger event; and
means for adjusting one or more gas parameters of the pressurized flow of breathable gas as a function over time in accordance with a respiratory therapy regime, wherein the respiratory therapy regime dictates adjustments to the one or more gas parameters based on the detected trigger events.

10. The system of claim 9, wherein the means for detecting trigger events comprises one or both of:
  means for detecting an intersection of an estimated subject flow with a predicted subject flow, and/or
  means for detecting inspiration of a predetermined inhalation volume by the subject after a predetermined moment in time.

11. The system of claim 9, wherein the means for detecting one or both of an ineffective trigger event and/or a false trigger event includes:
  means for detecting the ineffective trigger event based on a comparison of a subject flow with a predetermined flow threshold; and/or
  means for detecting the false trigger event based on a comparison of an airway pressure with a predetermined pressure threshold.

12. The system of claim 9, wherein the means for adjusting the trigger sensitivity includes:
  means for reducing the trigger sensitivity responsive to a determination that a first quota for detections of false trigger events has been reached; and
  means for increasing the trigger sensitivity responsive to a determination that a second quota for detections of ineffective trigger events has been reached.

\* \* \* \* \*